United States Patent [19]

Linhart et al.

[11] 4,315,017
[45] Feb. 9, 1982

[54] TRIAZOLE DERIVATIVES

[75] Inventors: Friedrich Linhart, Heidelberg; Bernd Zeeh, Ludwigshafen; Heinrich Adolphi, Limburgerhof, all of Fed. Rep. of Germany

[73] Assignee: BASF Aktiengesellschaft, Fed. Rep. of Germany

[21] Appl. No.: 135,914

[22] Filed: Mar. 28, 1980

Related U.S. Application Data

[62] Division of Ser. No. 59,179, Jul. 20, 1979, abandoned.

[30] Foreign Application Priority Data

Jul. 28, 1978 [DE] Fed. Rep. of Germany ....... 2833194

[51] Int. Cl.³ ..................... A61N 43/48; A61N 43/64; A61N 43/172; A61N 47/10
[52] U.S. Cl. ................................. 424/269; 424/251; 424/273 P; 424/275; 424/278; 424/285; 424/300
[58] Field of Search ................................ 424/269, 300

[56] References Cited

U.S. PATENT DOCUMENTS 4,102,891 7/1978 Timmler et al. .................... 548/212

Primary Examiner—Stanley J. Friedman
Attorney, Agent, or Firm—Keil & Witherspoon

[57] ABSTRACT

Triazole derivatives of the formula

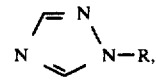

where R denotes benzyl substituted on the phenyl ring by linear or branched alkyl of 1 to 4 carbon atoms, 2-phenylvinyl which is unsubstituted or substituted by halogen on the phenyl ring, 3-phenyl-2-propenyl which is unsubstituted or substituted by halogen on the phenyl ring, 2-phenyl-2-propenyl which is unsubstituted or substituted by halogen on the phenyl ring, 1-phenylethyl, 3-phenylpropyl or 2-phenyl-2-chloroethyl, and salts thereof.

Insecticidal agents containing an insecticidal active ingredient selected from the group consisting of carbamates, phosphoric (phosphonic) (di) (thio) acid esters, pyrethrins, pyrethroids, α-alkylphenyl acetates, α-cyclopropylphenyl acetates and chlorinated hydrocarbons, and a triazole derivative of the formula I or a salt thereof, have a much stronger insecticidal action than insecticidal agents containing the individual components.

6 Claims, No Drawings

TRIAZOLE DERIVATIVES

This is a division of application Ser. No. 59,179 filed July 20, 1979, now abandoned.

The present invention relates to new triazole derivatives, their manufacture, and insecticidal agents containing insecticidal active ingredients selected from the group consisting of carbamates, phosphoric (phosphonic) (di)(thio) acid esters, pyrethrins, pyrethroids, α-alkylphenyl acetates, α-cyclopropylphenyl acetates and chlorinated hydrocarbons, and, to increase the insecticidal action of these active ingredients, triazole derivatives.

It is known that, when chemical active ingredients are used to combat injurious organisms, mixtures thereof sometimes have a much greater effect than was to be expected from an addition of the individual actions. Such an increase in action is termed synergism. It is not necessary for the synergist itself to have a recognizable action on the organism to be combated.

For combating injurious insects, the synergists used almost exclusively in practice are piperonal derivatives. Piperonyl dioxide, which increases the action of pyrethrins, is of particular importance.

We have now found that new triazole derivatives of the formula

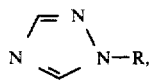

where R denotes benzyl substituted on the phenyl ring by linear or branched alkyl of 1 to 4 carbon atoms, 2-phenylvinyl which is unsubstituted or substituted by halogen on the phenyl ring, 3-phenyl-2-propenyl which is unsubstituted or substituted by halogen on the phenyl ring, 2-phenyl-2-propenyl which is unsubstituted or substituted by halogen on the phenyl ring, 1-phenylethyl, 3-phenylpropyl or 2-phenyl-2-chloroethyl, and salts thereof, considerably increase the action of insecticidal active ingredients selected from the group consisting of carbamates, phosphoric (phosphonic) (di) (thio) acid esters, pyrethrins, pyrethroids, α-alkylphenyl acetates, α-cyclopropylphenyl acetates and chlorinated hydrocarbons; insecticidal agents containing, in addition to these active ingredients, a triazole derivative of the formula I or a salt thereof thus have a considerably greater insecticidal action than insecticidal agents containing the individual components.

The triazole derivatives of the formula I and the salts thereof are extremely effective synergists having a wide area of action. In addition to a particularly strong synergistic action on carbamates, they increase the action of insecticides from the group consisting of phosphoric or phosphonic acid esters and the corresponding thio or dithio esters, pyrethrins, pyrethroids, α-alkylphenyl acetates, α-cyclopropylphenyl acetates and chlorinated hydrocarbons.

Suitable synergistic triazole derivatives of the formula I are 1,2,4-triazoles, or salts thereof, which bear, in the 1-position, benzyl mono- or polysubstituted on the phenyl ring by linear or branched alkyl of 1 to 4 carbon atoms, preferably in the 4-position, 1-phenylethyl, 2-phenyl-2-chloroethyl, 3-phenylethyl, 2-phenylvinyl, 3-phenyl-2-propenyl, or 2-phenyl-2-propenyl. The 2-phenylvinyl, 3-phenyl-2-propenyl and 2-phenyl-2-propenyl radicals may bear one or several halogen substituents, preferably chlorine or fluorine, and especially chlorine, on the phenyl nucleus.

Suitable salts of triazole derivatives of the formula I are those with inorganic or organic acids. Examples of such acids are hydrogen halides, especially hydrogen chloride and hydrogen bromide, nitric acid, sulfuric acid, oxalic acid, trichloroacetic acid, and aryl- or alkylsulfonic acids, especially p-toluenesulfonic acid and dodecylsulfonic acid.

Examples of triazoles suitable as synergists are 1-(4-methylbenzyl)-1,2,4-triazole, 1-(4-ethylbenzyl)-1,2,4-triazole, 1-(4-tert-butylbenzyl)-1,2,4-triazole, 1-(3-phenylpropyl)-1,2,4-triazole, 1-(1-phenylethyl)-1,2,4-triazole, 1-(3-phenyl-2-propenyl)-1,2,4-triazole, 1-(2-phenyl-2-propenyl)-1,2,4-triazole, 1-(2-phenyl-2-chloroethyl)-1,2,4-triazole, 1-[2-(2,4-dichlorophenyl)-vinyl]-1,2,4-triazole, and 1-[2-(4-fluorophenyl)-vinyl]-1,2,4-triazole, and salts, especially hydrochlorides, of these compounds.

Triazole derivatives of the formula I in which R denotes benzyl substituted on the phenyl ring by linear or branched alkyl of 1 to 4 carbon atoms, 3-phenyl-2-propenyl which is substituted or substituted by halogen on the phenyl ring, 2-phenyl-2-propenyl which is unsubstituted or substituted by halogen on the phenyl ring, 1-phenylethyl or 3-phenylpropyl, may be obtained in conventional manner by reaction of 1,2,4-triazole with the appropriate halides of the formula R-Hal, Hal denoting halogen and R having the above meanings. The reaction is carried out in the presence of an acid-binding agent, for example an organic base, such as triethylamine and N,N-dimethylaniline, or an inorganic base, for example an alkali metal carbonate or bicarbonate, such as sodium carbonate or bicarbonate, or potassium carbonate or bicarbonate, or an alkaline earth metal hydroxide, and in the presence of a solvent or diluent. Suitable solvents or diluents are esters, such as ethyl acetate; alcohols, such as methanol, ethanol, isobutanol and glycol; ketones, such as acetone and cyclohexanone; ethers, such as tetrahydrofuran and dioxane; toluene, acetonitrile, dimethylformamide and water.

Triazole derivatives of the formula I in which R denotes 2-phenylvinyl which is unsubstituted or substituted by halogen on the phenyl ring are obtained by reaction of compounds of the formula

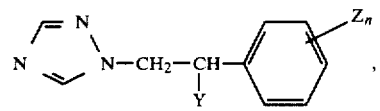

where Y and Z denote halogen, especially chlorine, and n denotes one of the integers, 0, 1 and 2, with a dehydrohalogenating agent, preferably a strong base, in the presence of a solvent or diluent. Suitable bases are alkali metal hydroxides, such as sodium and potassium hydroxide, alkali metal and alkaline earth metal alcoholates, such as sodium methylate, magnesium methylate and potassium tert-butylate, or organic bases, such as triethylamine. Suitable solvents or diluents are, in addition to water, especially alcohols, such as methanol; ethers, such as tetrahydrofuran and dioxane; methyl glycol and aprotic-dipolar solvents, such as dimethylformamide, acetonitrile, N-methylpyrrolidone and dimethyl sulfoxide.

Triazole derivatives of the formula I in which R denotes substituted 2-phenylvinyl may also be obtained by elimination of water or acid from compounds of the formula II in which Y denotes hydroxyl or esterified hydroxyl. Water or acid elimination is advantageously carried out with the aid of a strong acid or a base. Suitable acids are for example inorganic acids, such as sulfuric acid, hydrochloric acid and phosphoric acid, and aryl- or alkylsulfonic acids, such as p-toluenesulfonic acid, and suitable bases are alcoholates, such as alkali metal or alkaline earth metal alcoholates.

Compounds of the formula II in which Y denotes hydroxyl, Z denotes halogen and n denotes one of the integers 0, 1 and 2 may be prepared, by a reduction method conventionally used for ketones, from the corresponding triazolyl alkanones of the formula

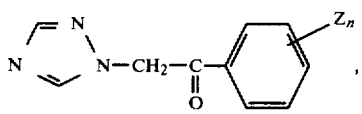

where Z and n have the above meanings. The compounds of the formula III are known and may be obtained by reaction of 1,2,4-triazole with compounds of the formula

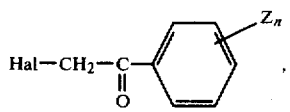

where Z and n have the above meanings and Hal denotes chlorine or bromine (German Laid-Open Application DE-OS No. 2,431,407).

The following examples illustrate the manufacture of the triazole derivatives of the formula I according to the invention.

EXAMPLE 1

30 parts by weight of 1-phenacyl-1,2,4-triazole is dissolved in 300 parts by weight of methanol; at 5° to 10° C., 5 parts by weight of sodium borohydride is added in portions. After the mixture has been brought to room temperature, about 20 parts by weight of ammonium chloride is added, and the mixture is acidified with dilute hydrochloric acid, heated to boiling, made alkaline with ammonia, and evaporated. The solid residue is slurried with water. Filtration gives 27.5 parts by weight of 1-[2-phenyl-2-hydroxyethyl]-1,2,4-triazole.

31 parts by weight of thionyl chloride is dripped into 25 parts by weight of 1-[2-phenyl-2-hydroxyethyl]-1,2,4-triazole, 300 parts by weight of chloroform and 1 part by weight of dimethylformamide; the mixture is refluxed until no more gas evolves. After the mixture has been cooled and filtered, the residue is washed with a small amount of chloroform and recrystallized from isopropanol. There is obtained 22.5 parts by weight of 1-[2-phenyl-2-chloroethyl]-1,2,4-triazole hydrochloride; m.p.: 178° C.

EXAMPLE 2

12.5 parts by weight of 1-(2-phenyl-2-chloroethyl)-1,2,4-triazole hydrochloride is suspended in methylene chloride and dilute ammonia is stirred in. The methylene chloride phase is separated, dried and evaporated. The residue is 9.6 parts of 1-(2-phenyl-2-chloroethyl)-1,2,4-triazole in the form of an oil.

Analysis: calc.: C 57.8; H 4.9; N 20.2; found: C 57.8; H 5.1; N 20.4.

EXAMPLE 3

20 parts by weight of a 30% strength sodium methylate solution is added to a solution of 15.6 parts by weight of 1-[2-(2,4-dichlorophenyl)-2-chloroethyl]-1,2,4-triazole hydrochloride in 100 parts by weight of methanol. The resultant mixture is refluxed for 5 hours, and then evaporated. 200 parts of water is added to the residue, and extraction carried out with 200 parts of dichloromethane. The extract is dried with sodium sulfate, evaporated and recrystallized from tetrachloromethane. Yield: 7.5 parts by weight of 1-[2-(2,4-dichlorophenyl)-vinyl]-1,2,4-triazole in the form of white needles; m.p.: 146° C.

EXAMPLE 4

A mixture of 14 parts by weight of 1,2,4-triazole, 200 parts by weight of acetonitrile, 32 parts by weight of potassium carbonate and 40 parts by weight of 3-phenylpropyl bromide is stirred for 12 hours. The mixture is then filtered and the filtrate is concentrated. Distillation gives 25 parts by weight of pure 1-(3-phenylpropyl)-1,2,4-triazole; b.p. (0.013 mbar): 114°–116° C.

EXAMPLE 5

14 parts by weight of 1,2,4-triazole, 200 parts by weight of acetonitrile, 32 parts by weight of potassium carbonate and 37 parts by weight of 4-methylbenzyl bromide are stirred for 12 hours. The residue is filtered, concentrated and dissolved in ethyl acetate. The 1-(4-methylbenzyl)-1,2,4-triazole hydrochloride (m.p. 155° C.) which precipitates out when hydrogen chloride is passed into the ethyl acetate solution is filtered off; yield: 31 parts by weight.

EXAMPLE 6

A mixture of 14 parts by weight of 1,2,4-triazole, 200 parts by weight of acetonitrile, 32 parts by weight of potassium carbonate and 39.2 parts by weight of cinnamyl chloride is stirred for 12 hours, and then filtered. The filtrate is concentrated, dissolved in dichloromethane, washed with water, evaporated and distilled. There is obtained 26 parts by weight of 1-(3-phenyl-2-propenyl)-1,2,4-triazole; b.p. (0.27 mbar): 130°–134° C.

The following compounds may be prepared analogously:

| | |
|---|---|
| 1-(4-ethylbenzyl)-1,2,4-triazole | b.p.(0.27 mbar) 122° C. |
| 1-(4-tert-butylbenzyl)-1,2,4-triazole | m.p. 35° C. |
| 1-(1-phenylethyl)-1,2,4-triazole | b.p.(0.13 mbar) 101°–102° C. |
| 1-(2-phenyl-2-propenyl)-1,2,4-triazole | b.p.(0.13 mbar) 125°–129° C. |
| 1-[2-(4-fluorophenyl)-vinyl]-1,2,4-triazole hydronitrate | m.p. 155° C. |

Examples of insecticidal active ingredients the effectiveness of which can be increased by the triazole derivatives of the formula I are carbamates, such as aryl-N-methylcarbamates, N,N-dimethylcarbamates of hydroxyheterocycles or of enols, oxime carbamates, e.g., 1-naphthyl-N-methylcarbamate, m-tolyl-N-methylcarbamate, 2-isopropylphenyl-N-methylcarbamate, 2-sec.-butylphenyl-N-methylcarbamate, 3-(1-methylbutyl)- phenyl-N-methylcarbamate, o-chlorophenyl-N-methylcarbamate, 3,4-dimethylphenyl-N-methylcarbamate, 3,5-diethylphenyl-N-methylcarbamate, 3-isopropyl-5-methylphenyl-N-methylcarbamate, 6-chloro-3,4-xylyl-N-methylcarbamate, 3,5-di-tert.-butylphenyl-N-methylcarbamate, 3,4,5-trimethylphenyl-N-methylcarbamate, 2-isopropylphenyl-N-methylcarbamate, 3,5-dimethyl-4-methylmercaptophenyl-N-methylcarbamate, 4-dimethylamino-m-tolyl-N-methylcarbamate, 4-dimethylamino-3,5-xylyl-N-methylcarbamate, 4-diallylamino-3,5-dimethylphenyl-N-methylcarbamate, 2-(1,3-dioxolan-2-yl)-phenyl-N-methylcarbamate, 4-benzothienyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 1-isopropyl-3-methyl-5-pyrazolyl-N,N-dimethylcarbamate, 2-dimethylcarbamoyl-3-methylpyrazolyl-(5)-N,N-dimethylcarbamate, 2-dimethylamino-5,6-dimethyl-4-pyrimidinyl-N,N-dimethylcarbamate, 2-(1-methoxy-2-chloro)-ethoxyphenyl-N-methylcarbamate, 3-[[(dimethylamino)-carbonyl]-oxy]-1,4-dimethyl-4-propyl-2-pyrazin-5-one, 2-methyl-2-(methylthio)-propionaldehyde-O-(methylcarbamoyl)-oxime, S-methyl-N-[(methylcarbamoyl)]oxy-thioacetamidate, S-2-cyanoethyl-N-[(methylcarbamoyl)-oxy]-thioacetimidate, methyl-N',N'-dimethyl-N-[(methylcarbamoyl)-oxy]-1-thiooxamidate, 2,4-dimethyl-1,3-dithiolane-2-carboxaldehyde-O-(methylcarbamoyl)-oxime, 3-(dimethylaminoethyleneimino)-phenyl-N-methylcarbamate, 4-(dimethylaminomethyleneimino)-m-tolyl-N-methylcarbamate, and 2-ethylthiomethylphenyl-N-methylcarbamate;

phosphoric or phosphonic acid esters and the corresponding thio or dithio esters, e.g. O,O-dimethyl-O-(1-methyl)-2-carbomethoxyvinyl)-phosphate, O,O-dimethyl-S-(N-methylcarbamoylmethyl)-phosphorodithioate, O,O-dimethyl-S-(N-methoxyethylcarbamoylmethyl)-phosphorodithioate, O,O-dimethyl-S-(N-formyl-N-methylcarbamoylmethylphosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-dimethyl-S-(ethylthio)-methylphosphorodithioate, O,O-diethyl-S-[(p-chlorophenylthio)methyl]-phosphorodithioate, O,O-dimethyl-S-(2-ethylthioethyl)phosphorothioate, O,O-dimethyl-S-(2-ethylthioethyl)-phosphorodithioate, O,O-dimethyl-S-(2-ethylsulfinylethyl)-phosphorothioate, O,O-diethyl-S-(2-ethylthioethyl)-phosphorodithioate, O,O-diethylthiophosphoryliminiphenyl acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiodiazol-5-[4H]-onyl-(4)methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyridinyl-(6)]-phosphorothioate, O,O-diethyl-O-[(2-diethylamino)-6-methyl-4-pyrimidinyl]-thionophosphate, O,O-dimethyl-S-(4-oxo-1,2,3-benzotriazin-3-yl-methyl)-phosphorodithioate, O,O-dimethyl-S-[(4,6-diamino-1,3,5-triazin-2-yl)]-methyl phosphorodithioate, O,O-diethyl-(1-phenyl-1,2,4-triazol-3-yl)-thionophosphate, O,S-dimethylphosphoramidothioate, O,S-dimethyl-N-acetylphosphoramidothioate, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl)-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methylthiophenyl)-phosphorothioate, O-ethyl-O-(3-methyl-4-methyltthiophenyl)-isopropylphosphororamidate, O,O-diethyl-O-[p-(methylsulfinyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[2-chloro-1-(2,4,5-trichlorophenyl)]-vinylphosphate, O,O-dimethyl-S-(1-phenyl)-ethyl acetate phosphorodithioate, bis-(dimethylamino)-fluorophosphine oxide, octamethylpyrophoramide, O,O,O,O-tetraethyldithiopyrophosphate, S-chloromethyl-O,O-diethylphosphorodithioate, O-ethyl-S,S-dipropyl-phosphorodithioate, O,O-dimethyl-O-2,2-dichlorovinyl-phosphate, O,O-dimethyl-1,2-dibromo-2,2-dichloroethylphosphate, O,O-dimethyl-2,2,2-trichloro-1-hydroxoethyl phosphonate, and O,O-dimethyl-S-[1,2-biscarbethoxyethyl-(1)]-phosphorodithioate;

pyrethrins, e.g., an active ingredient mixture consisting of pyrethrin I, pyrethrin II, cinerin I and cinerin II from Chrysanthemum cinerae folium flowers;

synthetic pyrethroids, such as esters of 2,2-dimethyl-3-(2,2-dimethylvinyl)-chloropropanecarboxylic acid, e.g., 2-allyl-3-methylcyclopenten-(2)-on-1-yl-(4)-chrysanthemate, 3,4,5,6-tetrahydrophthalimidomethyl-DL-cis,trans-chrysanthemate, 5-benzylfuryl-(3-methyl-DL-cis,trans-chrysanthemate, and 2-methyl-5-(2-propynyl)-3-furylmethyl-chrysanthemate, or esters of 2,2-dimethyl-3-(2,2-dihalovinyl)-cyclopropanecarboxylic acid, e.g., 3-phenoxybenzyl (±)-cis,trans-2,2-dimethyl-3-(2,2-dichlorovinyl)-cyclopropane-1-carboxylate, α-cyano-3-phenoxybenzyl (±)-cis,trans-2,2-dimethyl-3-(2,2-dichlorovinyl)-cyclopropanecarboxylate, and (s)-α-cyano-3-phenoxybenzyl-cis(1R, 3R)-2,2-dimethyl-3-(2,2-dibromovinyl)-cyclopropanecarboxylate;

α-alkylphenyl acetates, e.g., α-isopropylphenyl acetate, especially α-cyano-3-phenoxybenzyl-α-isopropyl-4-chlorophenyl acetate, 3-phenoxybenzyl-α-isopropyl-4-chlorophenyl acetate, 5-benzyl-3-furylmethyl-α-isopropyl-4-chlorophenyl acetate, 5-benzyl-3-furylmethyl-α-isopropyl-4-methylphenyl acetate, 3-phenoxybenzyl-α-isopropyl-4-methylphenyl acetate, 3-phenoxybenzyl-α-isopropyl-4-methoxyphenyl acetate, and 5-benzyl-3-methylfuryl-α-isopropyl-4-methoxyphenyl acetate;

α-cyclopropylphenyl acetates, e.g., α-cyano-3-phenoxybenzyl-α-cyclopropyl-4-chlorophenyl acetate, 5-benzyl-3-furylmethyl-α-cyclopropyl-4-chlorophenyl acetate, and α-cyano-3-phenoxybenzyl-α-cyclopropyl-4-bromophenyl acetate;

and chlorinated hydrocarbons, e.g., γ-hexachlorocyclohexane, 1,1-di-(p-methoxyphenyl)-2,2,2-trichloroethane, and 6,7,8,9,10,10-hexachloro-1,5,5a,6,9,9a-hexahydro-6,9-methano-2,4,3-benzodioxathiepin-3-oxide.

Triazole derivatives, or salts thereof, and insecticidal active ingredients may be employed in the agents according to the invention in relatively wide ratios. However, a ratio outside the range of from 1:10 to 10:1 parts by weight will probably seldom be of use. The preferred ratio range is from 1:5 to 5:1 parts by weight.

The insecticidal agents according to the invention may be used on a variety of plant and household pests. They may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used. Triazole derivatives and insecticidal active ingredient, or formulations thereof, may be applied separately or together.

The formulations generally contain from 0.1 to 95, and preferably 0.5 to 90%, by weight of active ingredient and synergist.

The amount of synergist and active ingredient in the ready-to-use formulations may vary within a wide range; it is generally from 0.0001 to 10%, preferably from 0.01 to 1%.

The agents according to the invention may also be successfully used in the ultra-low volume method, where it is possible to apply formulations containing more than 95% of synergist and active ingredient, or even a mixture consisting just of synergist and active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidione, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalane derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcool, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite wate liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

There may be added to the agents according to the invention (if desired, immediately before use (tankmix) oils of various types, herbicides, fungicides, other insecticides, and bactericides. These agents may be added to the agents according to the invention in a ratio by weight of from 1:10 to 10:1.

The use of the insecticidal agents according to the invention facilitates the control of plant and household pests. Examples of these are injurious insects from the Lepidoptera order, e.g., *Plutella maculipennis, Leucoptera coffeella, Hyponomeuta malinellus, Argyresthia conjugella, Sitotroga cerealalla, Phthorimea operculella, Capua reticulana, Sparganothis pilleriana, Cacoecia murinana, Tortrix viridana, Clysia ambiguella, Evetria buoliana, Polychrosis botrana, Cydia pomenella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymatria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibbialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Myetiola destructor, Dasyneura brassicae, Contarinia tritici, Haplodiplosis equestris, Tripula paludosa, Tipula oleracea, Dacus cucurbitae, Dacus oleae, Ceratitis capitata, Rhagoletis cerasi, Rhagoletis pomonella, Anastrepha ludens, Os-*

*cinella frit, Phorbia coarctata, Phorbia antiqua, Phorbia brassicae,* and *Pegomya hyoscyami;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucoterus, Dysdercus cingulatus, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae,* and *Megoura viciae;* and mites and ticks (Acarina) belonging to the Arachnida class, e.g., *Tetranychus urticae, Tetranychus atlanticus, Tetranychus pacificus, Paratetranychus pilosus, Bryobia praetiosa, Ixodes ricinus; Ornithodorus moubata, Ablyomma americanum, Dermacentor silvarum,* and *Boophilus microplus.*

The following biological experiments demonstrate the synergistic action. However, they should only be considered as examples, and in no way cover the whole range claimed.

The synergists employed are as follows:

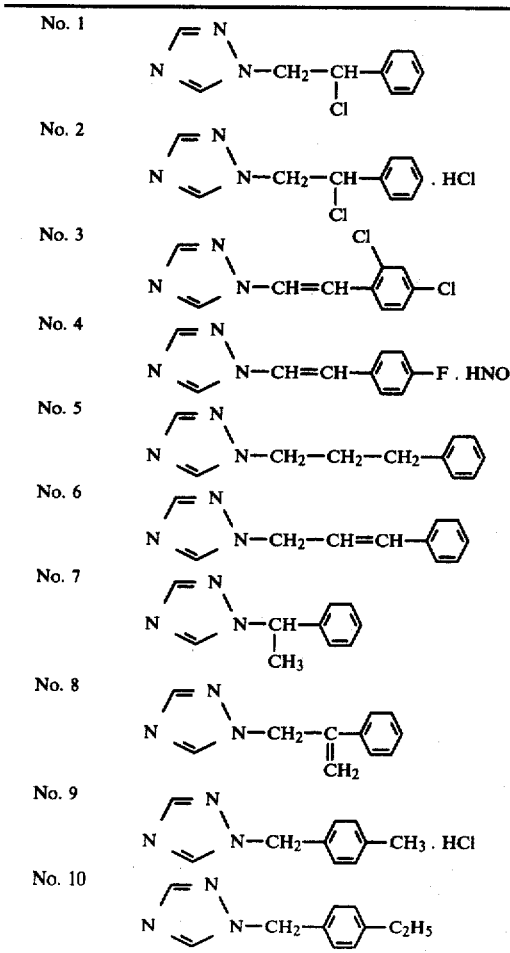

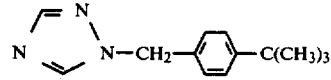

The insecticidal active ingredients employed were 1-naphthyl-N-methylcarbamate (carbaryl), 2,5-diethyl-phenyl-N-methylcarbamate (fenethcarb), 2-dimethylamino-5,6-dimethyl-4-pyrimidinyl-N,N-dimethylcarbamate (pirimicarb), O,O-dimethyl-S-1,2-bis-carbethoxyethyl-(1)]-phosphorodithioate (malathion), DL-2-allyl-3-methylcyclopenten-2-on-(1)-yl-(4)-DL-cis,trans-chrysanthemate (allethrin), and an active ingredient mixture consisting of pyrethrin I, pyrethrin II, cinerin I and cinerin II from Chrysanthemum cinerae folium flowers (hereinafter designated "pyrethrins").

EXAMPLE A

Synergistic action on oriental cockroaches (*Blatta orientalis*)

The bottom of 1-liter jars is treated with acetonic solutions of the insecticidal active ingredients and the synergists in the ratios given in the table below. After the solvent has evaporated, 5 adult cockroaches (*Blatta orientalis*) are placed in each jar, and the kill rate is determined after 48 hours.

The application rates are in logarithmic progression and permit a dose-effect curve to be drawn; the $LD_{50}$ is determined graphically and serves as a basis for assessment.

The insecticides used are carbaryl, fenethcarb, pirimicarb, malathion and allethrin; the ratio of insecticide to synergist is 1:5 parts by weight.

| Active ingredient | LD 50 | |
|---|---|---|
| No. 1 | >5.0 | mg |
| No. 2 | >5.0 | mg |
| No. 3 | >5.0 | mg |
| No. 4 | >5.0 | mg |
| No. 5 | >2.0 | mg |
| No. 6 | 9.0 | mg |
| No. 7 | >2.0 | mg |
| No. 8 | 9.0 | mg |
| No. 9 | >2.0 | mg |
| No. 10 | >2.0 | mg |
| No. 11 | >10.0 | mg |
| Carbaryl | 0.25 | mg |
| Carbaryl + No. 1 | 0.25 | mg + 1.25 mg |
| Carbaryl + No. 2 | 0.026 | mg + 0.13 mg |
| Carbaryl + No. 3 | 0.04 | mg + 0.2 mg |
| Carbyryl + No. 4 | 0.02 | mg + 0.01 mg |
| Carbaryl + No. 5 | 0.015 | mg + 0.075 mg |
| Carbaryl + No. 7 | 0.012 | mg + 0.06 mg |
| Carbaryl + No. 9 | 0.018 | mg + 0.09 mg |
| Carbaryl + No. 10 | 0.015 | mg + 0.075 mg |
| Fenethcarb | 0.45 | mg |
| Fenethcarb + No. 1 | <0.02 | mg + 0.1 mg |
| Fenethcarb + No. 2 | 0.13 | mg + 0.65 mg |
| Fenethcarb + No. 3 | 0.035 | mg + 0.175 mg |
| Fenethcarb + No. 5 | 0.24 | mg + 1.2 mg |
| Fenethcarb + No. 6 | 0.2 | mg + 1.0 mg |
| Fenethcarb + No. 7 | 0.11 | mg + 0.55 mg |
| Fenethcarb + No. 8 | 0.14 | mg + 0.7 mg |
| Fenethcarb + No. 9 | 0.16 | mg + 0.8 mg |
| Fenethcarb + No. 10 | 0.24 | mg + 1.2 mg |
| Fenethcarb + No. 11 | 0.12 | mg + 0.6 mg |
| Pirimicarb | 30 | mg ineffective |
| Pirimicarb + No. 5 | 0.11 | mg + 0.55 mg |
| Pirimicarb + No. 6 | 1.2 | mg + 6.0 mg |
| Pirimicarb + No. 7 | 0.45 | mg + 2.25 mg |
| Pirimicarb + No. 8 | 0.25 | mg + 1.25 mg |
| Pirimicarb + No. 10 | 0.65 | mg + 3.25 mg |

-continued

| Active ingredient | LD 50 | |
|---|---|---|
| Pirimicarb + No. 11 | 0.7 | mg + 3.5 mg |
| Malathion | 0.12 | mg |
| Malathion + No. 3 | 0.09 | mg + 0.45 mg |
| Malathion + No. 7 | 0.09 | mg + 0.45 mg |
| Malathion + No. 9 | 0.08 | mg + 0.4 mg |
| Allethrin | 0.11 | mg |
| Allethrin + No. 1 | 0.021 | mg + 0.105 mg |
| Allethrin + No. 2 | 0.021 | mg + 0.105 mg |
| Allethrin + No. 3 | 0.045 | mg + 0.225 mg |
| Allethrin + No. 5 | 0.034 | mg + 0.17 mg |
| Allethrin + No. 6 | 0.06 | mg + 0.3 mg |
| Allethrin + No. 7 | 0.04 | mg + 0.2 mg |
| Allethrin + No. 8 | 0.024 | mg + 0.12 mg |
| Allethrin + No. 9 | 0.04 | mg + 0.2 mg |
| Allethrin + No. 10 | 0.04 | mg + 0.2 mg |
| Allethrin + No. 11 | 0.024 | mg + 0.12 mg |

EXAMPLE B

Synergistic action on houseflies (*Musca domestica*); continuous contact

Both covers and bottoms of Petri dishes 10 cm in diameter are lined with a total per dish of 2 ml of acetonic solutions of the active ingredients. After the solvent has evaporated (about 30 mins.), 10 flies are introduced into each dish.

The kill rate is determined after 4 hours and the LD$_{50}$ is determined graphically.

| Active ingredient | LD 50 | |
|---|---|---|
| Pyrethrins | 0.015 | mg |
| No. 1 | >2.0 | mg |
| Pyrethrins + No. 1 | 0.0055 | mg + 0.0275 mg |
| No. 2 | 0.2 | mg |
| Pyrethrins + No. 2 | 0.006 | mg + 0.03 mg |
| No. 4 | >2.0 | mg |
| Pyrethrins + No. 4 | 0.005 | mg + 0.025 mg |

EXAMPLE C

Contact action on houseflies (*Musca domestica*)

1 μl of the active ingredient dissolved in acetone is administered to the ventral abdomen of 4-day old imagoes under slight CO$_2$ narcosis. 20 animals treated in the same way are then placed in a cellophane bag having a volume of approximately 500 ml.

After 4 hours the kill rate is determined, a dose-mortality curve is drawn from the different concentrations, and the LD$_{50}$ is worked out.

| Active ingredient | LD$_{50}$ |
|---|---|
| Pyrethrins | 0.1 μg/fly |
| No. 5 | 10 μg/fly ineffective |
| Pyrethrins + No. 5 | 0.035 + 0.35 μg/fly |

EXAMPLE D

Synergistic action on granery weevils (*Sitophilus granarius*)

Petri dishes 10 cm in diameter are lined with acetonic solutions of the active ingredients. After the solvent has evaporated, 50 granary weevils are placed in each dish.

After 4 hours, the weevils are transferred to untreated vessels. The kill rate is determined after 24 hours, by counting how many weevils are, after this period has elapsed, capable of leaving an untreated cardboard dish (40 mm in diameter, 10 mm high) within 60 minutes.

| Active ingredient | LD 50 | |
|---|---|---|
| Carbaryl | 2.5 | mg |
| No. 1 | 2 | mg ineffective |
| Carbaryl + No. 1 | 0.17 | mg + 0.85 mg |
| No. 5 | 2 | mg ineffective |
| Carbaryl + No. 5 | 0.085 | mg + 0.425 mg |
| No. 6 | 2 | mg ineffective |
| Carbaryl + No. 6 | 1 | mg + 1 mg (kill rate >95%) |
| No. 8 | 2 | mg ineffective |
| Carbaryl + No. 8 | 0.23 | mg + 1.15 mg |
| No. 9 | 4 | mg ineffective |
| Carbaryl + No. 9 | 0.52 | mg + 2.6 mg |
| No. 10 | 2 | mg ineffective |
| Carbaryl + No. 10 | 0.17 | mg + 0.85 mg |
| No. 11 | 2 | mg ineffective |
| Carbaryl + No. 11 | 1 | mg + 1 mg (kill rate >95%) |

| Active ingredient | LD 50 | |
|---|---|---|
| Pyrethrins | 1.2 | mg |
| No. 1 | 1 | mg ineffective |
| Pyrethrins + No. 1 | 0.15 | mg + 0.75 mg |
| No. 5 | 2 | mg ineffective |
| Pyrethrins + No. 5 | 0.07 | mg + 0.35 mg |

EXAMPLE E

Synergistic action on houseflies (*Musca domestica*; dip experiment)

100 ml of aqueous active ingredient formulations (active ingredient concentration in %) is poured over 20 adult houseflies (*Musca domestica*) on a filter in a nutsch (15 cm in diameter). A gauze lid prevents the animals from surfacing during treatment. After 5 seconds the formulation is filtered off and the flies are transferred to clean Petri dishes (10 cm in diameter) on the bottom of which a round filter paper has been placed.

The animals in supine position are counted after 4 and 24 hours.

Results

| Active ingredient | LD 50 after 4 hours | LD 50 after 24 hours |
|---|---|---|
| Pirimicarb | 0.05% | 0.04% |
| No. 1 | 0.085% | 0.05% |
| Pirimicarb + No. 1 | 0.0025% + 0.0125% | <0.0025% + 0.0125% |
| No. 2 | 0.2% ineffective | 0.1% |
| Pirimicarb + No. 2 | 0.004% + 0.02% | <0.004% + 0.02% |
| No. 3 | 0.2% | 0.05% |
| Pirimicarb + No. 3 | 0.0035% + 0.0175% | 0.0015% + 0.0075% |
| No. 5 | >0.2% | 0.05% |
| Pirimicarb + No. 5 | 0.01% + 0.05% 0.004% + 0.02% | |
| No. 6 | >0.2% | 0.07% |
| Pirimicarb + No. 6 | 0.009% + 0.045% | 0.004% + 0.02% |

We claim:

1. An insecticidal agent comprising an insecticidally active carbamate selected from the group consisting of 2,5-diethylphenyl-N-methylcarbamate, 1-naphthyl-N-methylcarbamate, m-tolyl-N-methylcarbamate, 2-isopropylphenyl-N-methylcarbamate, 2-sec.-butylphenyl-N-methylcarbamate, 3-(1-methylbutyl)-phenyl-N-methylcarbamate, o-chlorophenyl-N-methylcarbamate, 3,4-dimethylphenyl-N-methylcarbamate, 3,5-diethylphenyl-N-methylcarbamate, 3-isopropyl-5-methylphenyl-N-methylcarbamate, 6-chloro-3,4-xylyl-N-methylcarbamate, 3,5-di-tert.-butylphenyl-N-methylcarbamate, 3,4,5-trimethylphenyl-N-methylcarbamate, 2-isopropylphenyl-N-methylcarbamate, 3,5-dimethyl-4-methylmercaptophenyl-N-methylcarbamate, 4-dimethylamino-m-tolyl-N-methylcarbamate, 4-dimethylamino-3,5-xylyl-N-methylcarbamate, 4-diallylamino-3,5-dimethylphenyl-N-methylcarbamate, 2-(1,3-dioxolan-2-yl)-phenyl-N-methylcarbamate, 4-benzothienyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 1-isopropyl-3-methyl-5-pyrazolyl-N,N-dimethylcarbamate, 2-dimethylcarbamoyl-3-methylpyrazolyl-(5)-N,N-dimethylcarbamate, 2-dimethylamino-5,6-dimethyl-4-pyrimidinyl-N,N-dimethylcarbamate, 2-(1-methoxy-2-chloro)-ethoxyphenyl-N-methylcarbamate, 3-(dimethylaminoethyleneimino)-phenyl-N-methylcarbamate, 4-(dimethylaminomethyleneimino)-m-tolyl-N-methylarbamate, and 2-ethylthiomethylphenyl-N-methylcarbamate and a triazole derivative of the formula I as a synergist

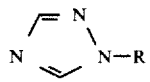

where R denotes benzyl substituted on the phenyl ring by linear or branched alkyl of 1 to 4 carbon atoms, 2-phenylvinyl which is unsubstituted or substituted by halogen on the phenyl ring, 3-phenyl-2-propenyl which is unsubstituted or substituted by halogen on the phenyl ring, 2-phenyl-2-propenyl which is unsubstituted or substituted by halogen on the phenyl ring, 1-phenylethyl, 3-phenylpropyl or 2-phenyl-2-chloroethyl, or a salt thereof, wherein the ratio of carbamate to triazole derivative of the formula I, or a salt thereof, is from 1:10 to 10:1 parts by weight.

2. An insecticidal agent as set forth in claim 1, wherein the carbamate is 1-naphthyl-N-methylcarbamate, 2,5-diethylphenyl-N-methylcarbamate or 2-dimethylamino-5,6-dimethyl-4-pyrimidinyl-N,N-dimethylcarbamate.

3. An insecticidal agent as set forth in claim 1, wherein the ratio of carbamate to triazole derivative of the formula I, or a salt thereof, is from 1:5 to 5:1 parts by weight.

4. A process for combating insects, wherein the insects or their biotope are treated with an insecticidally effective amount of an insecticidal agent containing an insecticidally active carbamate selected from the group consisting of 2,5-diethylphenyl-N-methylcarbamate, 1-naphthyl-N-methylcarbamate, m-tolyl-N-methylcarbamate, 2-isopropylphenyl-N-methylcarbamate, 2-sec.-butylphenyl-N-methylcarbamate, 3-(1-methylbutyl)-phenyl-N-methylcarbamate, o-chlorophenyl-N-methylcarbamate, 3,4-dimethylphenyl-N-methylcarbamate, 3,5-diethylphenyl-N-methylcarbamate, 3-isopropyl-5-methylphenyl-N-methylcarbamate, 6-chloro-3,4-xylyl-N-methylcarbamate, 3,5-di-tert.-butylphenyl-N-methylcarbamate, 3,4,5-trimethylphenyl-N-methylcarbamate, 2-isopropylphenyl-N-methylcarbamate, 3,5-dimethyl-4-methylmercaptophenyl-N-methylcarbamate, 4-dimethylamino-m-tolyl-N-methylcarbamate, 4-dimethylamino-3,5-xylyl-N-methylcarbamate, 4-diallylamino-3,5-dimethylphenyl-N-methylcarbamate, 2-(1,3-dioxolan-2-yl)-phenyl-N-methylcarbamate, 4-benzothienyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 1-isopropyl-3-methyl-5-pyrazolyl-N,N-dimethylcarbamate, 2-dimethylcarbamoyl-3-methylpyrazolyl-(5)-N,N-dimethylcarbamate, 2-dimethylamino-5,6-dimethyl-4-pyrimidinyl-N,N-dimethylcarbamate, 2-(1-methoxy-2-chloro)-ethoxyphenyl-N-methylcarbamate, 3-(dimethylaminomethyleneimino)-phenyl-N-methylcarbamate, 4-(dimethylaminomethyleneimino)-m-tolyl-N-methylcarbamate, and 2-ethylthiomethylphenyl-N-methylcarbamate and a triazole derivative of the formula I as a synergist

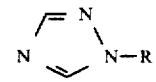

where R denotes benzyl substituted on the phenyl ring by linear or branched alkyl of 1 to 4 carbon atoms, 2-phenylvinyl which is unsubstituted or substituted by halogen on the phenyl ring, 3-phenyl-2-propenyl which is unsubstituted or substituted by halogen on the phenyl ring, 2-phenyl-2-propenyl which is unsubstituted or substituted by halogen on the phenyl ring, 1-phenylethyl, 3-phenylpropyl or 2-phenyl-2-chloroethyl or a salt thereof, the ratio of carbamate to triazole derivative of the formula I, or a salt thereof, being from 1:10 to 10:1 parts by weight.

5. A process as set forth in claim 4, wherein the insecticidally active carbamate is 1-naphthyl-N-methylcarbamate, 2,5-diethylphenyl-N-methylcarbamate or 2-dimethyl-5,6-dimethyl-4-pyrimidinyl-N,N-dimethylcarbamate.

6. A process ase set forth in claim 4, wherein the ratio of carbamate to triazole is from 1:5 to 5:1 parts by weight.

* * * * *